(12) United States Patent
Faris et al.

(10) Patent No.: US 10,876,096 B2
(45) Date of Patent: Dec. 29, 2020

(54) CELL CULTURE MEDIUM FOR ENHANCED HEPATOCYTE FUNCTION

(71) Applicants: Corning Incorporated, Corning, NY (US); Ronald Allen Faris, Elmira, NY (US); Yulong Hong, Painted Post, NY (US); Joydeep Lahiri, Painted Post, NY (US); Jin Liu, Painted Post, NY (US); Olivia Grace Weeks, Brookline, MA (US)

(72) Inventors: Ronald Allen Faris, Elmira, NY (US); Yulong Hong, Painted Post, NY (US); Joydeep Lahiri, Painted Post, NY (US); Jin Liu, Painted Post, NY (US); Olivia Grace Weeks, Brookline, MA (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 14/647,304

(22) PCT Filed: Nov. 25, 2013

(86) PCT No.: PCT/US2013/071636
§ 371 (c)(1),
(2) Date: May 26, 2015

(87) PCT Pub. No.: WO2014/085308
PCT Pub. Date: Jun. 5, 2014

(65) Prior Publication Data
US 2015/0291932 A1    Oct. 15, 2015

Related U.S. Application Data

(60) Provisional application No. 61/730,762, filed on Nov. 28, 2012.

(51) Int. Cl.
C12N 5/071 (2010.01)
C12Q 1/6876 (2018.01)
G01N 33/50 (2006.01)

(52) U.S. Cl.
CPC ........... *C12N 5/067* (2013.01); *C12Q 1/6876* (2013.01); *G01N 33/5067* (2013.01);
(Continued)

(58) Field of Classification Search
CPC ............... C12N 5/067; C12N 2503/02; C12N 2533/54; C12N 2501/727;
(Continued)

(56) References Cited

U.S. PATENT DOCUMENTS 6,303,652 B1 * 10/2001 Uckun ............... A61K 31/225
514/227.5
2005/0148073 A1    7/2005 Hansen et al.
(Continued)

FOREIGN PATENT DOCUMENTS

WO    9954286 A2    10/1999

OTHER PUBLICATIONS

Lan et al., Dissecting the phenotypes of Plk1 Inhibition in cancer cells using novel kinase inhibitory chemical CBB2001; Science, vol. 92, pp. 1503-1514, 2012.*
(Continued)

*Primary Examiner* — Marcia S Noble
*Assistant Examiner* — Lauren K Van Buren
(74) *Attorney, Agent, or Firm* — Annie J. Kock; Hallie W. O'Brien (57) ABSTRACT

Cell culture compositions containing LFM-A13 or a structurally related compound can enhance global hepatic function. For example, LFM-A13 is shown to enhance levels of a broad variety of drug metabolism enzymes, including CYP enzymes, and other hepatic enzymes. LFM-A13 is also
(Continued)

shown to promote differentiation of stem cells into hepatocytes. LFM-A13 and structurally related compounds can be used in cell culture to enhance global drug metabolism of liver cells for enhanced in vitro study the effects of drug metabolism on other candidate drug compounds.

19 Claims, 8 Drawing Sheets

(52) U.S. Cl.
CPC .. *C12N 2501/727* (2013.01); *C12N 2501/999* (2013.01); *C12N 2503/02* (2013.01); *C12N 2506/02* (2013.01); *C12N 2533/54* (2013.01); *C12Q 2600/158* (2013.01); *G01N 2333/90245* (2013.01)

(58) Field of Classification Search
CPC .......... C12N 2501/999; C12N 2506/02; C12Q 1/6876; C12Q 2600/158; G01N 33/5067; G01N 2333/90245
See application file for complete search history.

(56) References Cited

U.S. PATENT DOCUMENTS

| | | | |
|---|---|---|---|
| 2005/0170502 A1* | 8/2005 | Zern | C12N 5/067 435/370 |
| 2011/0071767 A1* | 3/2011 | Porter | G01N 33/5014 702/20 |
| 2011/0151561 A1 | 6/2011 | Davis et al. | |

OTHER PUBLICATIONS

Eagle, H., Amino acid metabolism in mammalian cell cultures; Science, vol. 130, pp. 432-437, 1959.*
Zanger et al., Cytochrome P450 enzymes in drug metabolism: Regulation of gene expression, enzyme activities, and impact of genetic variation; Pharmacology and Therapeutics vol. 138, pp. 103-141, 2013 (Year: 2013).*
Cowan et al; "Derivation of Embryonic Stem-Cell Lines From Human Blastocysts"; N Engl J Med 350; 13; Mar. 25, 2004; pp. 1353-1356.
English Translation of CN201380071463.0 Office Action dated May 10, 2017; 10 pages; Chinese Patent Office.
Fahmi et al; "Cytochrome P450 3A4 MRNA is a More Reliable Marker Than CYP3A4 Activity for Detecting Pregnane X Receptor-Activated Induction of Drug-Metabolizing Enzymes"; Drug Metabolism and Disposition, vol. 38, No. 9, pp. 1605-1611, 2010.
Genbacev et al; "Serum-Free Derivation of Human Embryonic Stem Cell Lines on Human Placental Fibroblast Feeders"; Fertility and Sterility, vol. 83, Issue 5, May 2005, pp. 1517-1529.
Hosomi et al; "Development of a Highly Sensitive Cytotoxicity Assay System for CYP3A4-Mediated Metabolic Activation"; Published May 3, 2011; Drug Metabolism and Toxicology, Faculty of Pharmaceutical Sciences, Kanazawa University, Kakuma-Machi Kanazawa Japan; 37 pages.
Hu et al; "Induction of CYP1A1 is a Nonspecific Biomarker of Aryl Hydrocarbon Receptor Acivation: Results of Large Scale Screening of Pharmaceuticals and Toxicants in Vivo and in Vitro"; Molecular Pharmacology, 79; 1475-1486, 2011.
International Search Report and Written Opinion of the International Searching Authority; PCT/US2013/071636; dated Jan. 17, 2014; 12 pages; European Patent Office.
Klimanskaya et al; "Human Embryonic Stem Cells Derived Without Feeder Cells"; Lancet 2005; 365; 1636-1641.
Munier-Lehmann et al; "On Dihydroorotate Dehydrogenases and Their Inhibitors and Uses"; Journal of Medicinal Chemistry; Mar. 2013; DOI:10.1021/JM301848W; 21 pages.
Sugatani et al; "Induction of UGT1A1 and CYP2B6 by an Antimitogenic Factor in HEPG2 Cells is Mediated Through Suppression of Cyclin-Dependent Kinase 2 Activity: Cell Cycle-Dependent Expression"; Druct Metabolism and Disposition; vol. 38, No. 1; pp. 177-186; 2010.
Takahashi et al; "Induction of Pluripotent Stem Cells From Adult Human Fibroblasts by Defined Factors"; Cell, 131, 861-872, Nov. 30, 2007.
Thomson et al; "Embryonic Stem Cell Lines Derived From Human Blastocysts"; Science; vol. 282, Nov. 6, 1998; pp. 1145-1147.
Wikipedia; Glass Transition; Downloaded Jun. 18, 2015, http://en.wikipedia.org/wiki/glass_transition; 12 pages.
Yao et al; "The Active Metabolite of Leflunomide A771726 Inhibits Proliferation and Collagen Synthesis of Hepatic Stellate Cell"; Journal of Zhejiang University (Medical Sciences) vol. 33, No. 6 pp. 515-518; 2004.
Yu et al; "Induced Pluripotent Stem Cell Lines Derived From Human Somatic Cells"; Science; Dec. 21, 2007; vol. 318, Issue 5858; pp. 1917-1920.
Wijayanti et al: "Inhibition of phorbol ester-dependent peroxiredoxin I gene activation by lipopolysaccharide via phosphorylation of RelA/p65 at serine 276 in monocytes", Free Radical Biology and Medicine, Elsevier Science, US, vol. 44, No. 4, Nov. 17, 2007 (Nov. 17, 2007), pp. 699-710, XP022437227, ISSN: 0891-5849 the whole document.
Vrenken T E et al: "The active metabolite of leflunomide, A77 1726, protects rat hepatocytes against bile acid-induced apoptosis", Jornal of Hepatology, Elsevier, Amsterdam, NL, vol. 49, No. 5, Nov. 1, 2008 (Nov. 1, 2008), pp. 799-809, XP025587136, ISSN: 0168-8278, DOI: 10.1016/J.JHEP.2008.07.019 [retrieved on Aug. 22, 2008] the whole document.
Shi et al: "Hepatic Cytochrome p450s Attenuate the Cytotoxicity Induced by Leflunomide and Its Active Metabolite A77 1726 in Primary Cultured Rap Hepatocytes", Toxicological Sciences, vol. 122, No. 2, May 4, 2011 (May 4, 2011), pp. 579-586, XP055095241, ISSN: 1096-6080, DOI: 10.1093/toxsci/kfr106 the whole document.
Lesser KE, Allen PD, Woolhandler SJ. Himmelsterin DU, Wolfe SM and Bor DH (2002). Timing of New Black Box Warnings and Withdrawals for Prescription Medications. JAMA. 287: 2215-2220.
Guillouzo A (1998). Liver Cell Models in in Vitro Toxicology. Environmental Health Perspectives. vol. 106, Supplement 2: 511-532.
Maslansky CJ and Williams GM (1982). Primary Cultures and the Levels of Cytochrome P-450 in Hepatocytes from Mouse, Rat, Hamster and Rabbit Liver. In Vitro. 18: 663-693.
Pondugula, SR, Dong H. and Chen T (2009). Phosphorylation and protein-protein interactions in PXR-mediated CYP3A repression. Expert Opinion in Drug Metabolism Toxicology. 5(8), 861-873.
Ding X. and Staudinger JL.(2005). Induction of Drug Metabolism by Forskolin: The Role of the Pregnane X Receptor and the Protein Kinase A Signal Transduction Pathway. J. Pharmacol Exp. Ther. 312 (2):849-56.
Ding, X and Staudinger J.L. (2004). Repression of PXR-mediated induction of hepatic CYP3A gene expression by protein kinase C.
Watanabe, K. et al. A Rock inhibitor permits survival of dissociated human embryonic stem cells. Nat. Biotechnol.; 25, 681-686 (2007).
Tallantyre E, Evangelou N, Constantinescu CS (2008). Spotlight on teriflunomide. Int MS J. 15(2):62-8.
Kalgutkar AS et al. (2003). In vitro metabolism studies on the isoxazole ring scission in the anti-inflammatory agent lefluomide to its active α-cyanoenol metabolite A771726: mechanistic similarities with the cytochrome P450-catalyzed dehydration of aldoximes. Drug Metab. And Depos. 31, 1240-1250.
Leban J, Vitt D.(2011). Human dihydroorotate dehydrogenase inhibitors, a novel approach for the treatment of autoimmune and inflammatory diseases. Arzneimittelforschung. 61(1):66-72.
Mahajan S, Ghosh S, Sudbeck EA, Zheng Y, Downs S, Hupke M, Uckun FM (1999). Rational design and synthesis of a novel anti-leukemic agent targeting Bruton's tyrosine kinase (BTK), LFM-A13 [alpha-cyano-beta-hydroxy-beta-methyl-N-(2, 5-dibromophenyl)propenamide]. J Biol Chem. 274(14):9587-99.

(56) References Cited

OTHER PUBLICATIONS

Uckun FM (2007). Chemosensitizing anti-cancer activity of LFM-A13, a leflunomide metabolite analog targeting polo-like kinases. Cell Cycle. 6(24):3021-6.
Li EK, Tam LS, Tomlinson B (2004). Leflunomide in the treatment of rheumatoid arthritis. Clinical Therapy. 26(4):447-59.

* cited by examiner

CELL CULTURE MEDIUM FOR ENHANCED HEPATOCYTE FUNCTION

CROSS-REFERENCE TO RELATED APPLICATION

This application claims the benefit of priority under 35 U.S.C. §119 of U.S. Provisional Application Ser. No. 61/730,762, filed on Nov. 28, 2012, the content of which is relied upon and incorporated herein by reference in its entirety.

FIELD

The present disclosure relates to cell culture media, particularly cell culture media useful for culturing hepatocytes or liver cells, and methods of use thereof.

BACKGROUND

Drug induced liver injury is one of the main causes of drug withdrawal from the market, accounting for about 30% of the drugs withdrawn from the market. Today, accurate prediction of drug induced liver injury remains a major challenge to drug development. Before being approved for clinical trial, drug candidates are typically tested for drug induce liver injury in various in vitro liver cell models, such as primary hepatocytes (PHHs) and liver cell lines. Although PHHs are currently used as the "Gold Standard" for drug induced liver injury study, maintenance of the function of PHHs in vitro can be difficult. For example, some of the key liver functions of PHHs, such as phase I/II drug metabolism enzyme activity, decrease by approximately 50% during the first 24 to 48 hours in culture. In addition, donor-to-donor variation and limited supplies prevent PHH from being used in early stage drug toxicity studies, such as high throughput screening (HTS). Liver cell lines possess some advantages relative to PHHs. For example, liver cell lines are usually available in large numbers with unlimited sub-cultivation, are easy to manipulate and are amenable to high-throughput screening. However, liver cell lines do suffer from some disadvantages relative to PHHs, such as much lower levels of drug metabolism enzymes. Since the viability and function of hepatocytes are largely determined by their culture conditions, improvement of cell culture medium to support highly functional hepatocytes is highly desired.

In the body, survival, proliferation, differentiation and metabolism functions of hepatocytes are highly regulated by a variety of soluble factors. These soluble factors are lost after hepatocytes are isolated from liver tissue. Upon isolation, primary hepatocytes enter a de-differentiation state and gradually lose most of their functions. Through decades of research, some of the soluble factors that maintain hepatocyte function, such as insulin, hepatocyte growth factor, hormones, and the like have been identified and characterized. These soluble factors modulate hepatocyte functions through different mechanisms, such as signal transduction pathways, cell cycle controls, and the like. Addition of these soluble factors to cell culture medium has significantly improved hepatocyte viability and function. However, the in vivo function of hepatocytes is not fully restored even in the presence of these soluble factors in culture medium.

The function of cultured primary hepatocytes can be modulated by small molecule chemicals. For example, the expression and function of CYP3A4 can be enhanced by protein kinase A activators, but are repressed by protein kinase C activators. Therefore, any small molecule chemicals that have the ability to mimic the regulatory functions of soluble factors in human body and to enhance global hepatocyte functions could potentially be used as a component in cell culture medium. While it has been suggested that protein kinase A (PKA) inhibitors can be used in cell culture medium to promote primary human hepatocyte growth, there is no report, however, with respect to the culture medium containing small molecules PKA inhibitors to enhance hepatocyte function.

Cyclin dependent kinase inhibitors have been shown to enhance the expression of a number of hepatic enzymes including CYP2B6 and UGT1A1 in HepG2 cells, but not in HuH6 human hepatoblastoma cells (Sugatani et al., Drug Metabolism and Disposition 38: 177-186, 2010), but have not been suggested as agents for enhancing global hepatic function.

BRIEF SUMMARY

The present disclosure describes, among other things, compounds, compositions, and methods that can enhance global drug metabolism function of cells in culture. For example, increased expression of a broad variety of drug metabolism enzymes can be obtained by culturing hepatocytes or liver cell lines in medium containing compounds as described herein; particularly LFM-A13 and structurally related compounds. As described herein, it has been found that LFM-A13, which has been reported to be a potent Burton's tyrosine kinase (BTK) inhibitor, induces broad expression of drug metabolism enzymes, such as cytochrome P450 (CYP) enzymes, in cultured hepatocytes. In addition, LFM-A13 and structurally related compounds can also enhance other hepatic functions. Surprisingly, structurally unrelated BTK inhibitors were tested and did not produce results similar to LFM-A13.

In embodiments described herein a cell culture composition can include LFM-A13 or a structurally related compound. The composition can be used to enhance global metabolic function of cultured liver cells, to maintain the hepatic function of cultured liver cells, or to differentiate stem cells into hepatocytes. Accordingly, such cell culture compositions can be used for cultivation of high functional human liver cells for drug discovery. The restoration or maintenance of higher drug metabolism function can lead to better cell based models to improve the prediction of drug induced liver injury.

Advantages of one or more of the various embodiments presented herein over prior cell culture compositions and methods will be readily apparent to those of skill in the art based on the following detailed description when read in conjunction with the accompanying drawings.

DETAILED DESCRIPTION

In the following detailed description and examples, reference is made to the accompanying drawings that form a part hereof, and in which are shown by way of example results of several specific experiments that illustrate the effects of the compounds, compositions, and methods described herein. It is to be understood that other embodiments are contemplated and can be made without departing from the scope or spirit of the present disclosure. The following detailed description and examples, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a," "an," and "the" encompass embodiments having plural referents, unless the content clearly dictates otherwise.

As used in this specification and the appended claims, the term "or" is generally employed in its sense including "and/or" unless the content clearly dictates otherwise.

As used herein, "stem cells" are cells that have the ability to continuously divide (self-renewal) and that are capable of differentiating into a diverse range of specialized cells. In some embodiments, the stem cells are multipotent, totipotent, or pluripotent stem cells that can be isolated from an organ or tissue of a subject. Such cells are capable of giving rise to fully differentiated or mature cell types. A stem cell can be a bone marrow-derived stem cell, mesenchymal stem cells (MSC), autologous or otherwise, a neuronal stem cell, or an embryonic stem cell. A stem cell can be a multi-lineage cell derived from epithelial and adipose tissues, umbilical cord blood, liver, brain or other organ. In various embodiments, the stem cells are pluripotent stem cells, such as pluripotent embryonic stem cells isolated from a mammal. Suitable mammals can include rodents such as mice or rats, primates including human and non-human primates.

Examples of human embryonic stem cell lines that have been established include, but are not limited to, H1, H7, H9, H13 or H14 (available from WiCell established by the University of Wisconsin) (Thompson (1998) Science 282: 1145); hESBGN-01, hESBGN-02, hESBGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5): 1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells can also be obtained directly from primary embryonic tissue. Typically this is done using frozen in vitro fertilized eggs at the blastocyst stage, which would otherwise be discarded.

Other sources of pluripotent stem cells include induced primate pluripotent stem (iPS) cells. iPS cells refer to cells, obtained from a juvenile or adult mammal, such as a human, that are reprogrammed to attain the phenotype of a pluripotent stem cell such as an hESC. Reprogramming can be accomplished by methods known to those skilled in the art. Cell reprogramming methods include but are not limited to methods that genetically modify cells, e.g., by transfection infection with one or more appropriate vectors, or methods that epigenetically modify cells, e.g., by exposure to small molecules such has histone deacetylase inhibitors. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm. The iPS cells, like hESC, also form teratomas when injected into immuno-deficient mice, e.g., SCID mice. (Takahashi et al., (2007) Cell 131(5):861; Yu et al., (2007) Science 318: 5858).

As used herein, a cultured "liver cell" is a cell isolated from liver; a cell derived from a cell isolated from liver and that has some hepatic function, such as drug metabolism function; or a progenitor cell, such as a stem cell differentiated into a liver cell or a cell that has some hepatic function, such as drug metabolism function. Other functions of a liver cell can include the production and secretion of plasma proteins, e.g., serum albumin, inter-alpha inhibitor protease, fibrinogen, lipoproteins, ceruloplasmin, transferrin, complement, immunoglobulins, and clotting factors.

A liver cell can be a hepatocyte, such as a primary hepatocyte, a cell of a liver cell line, such as a cell line derived from a hepatic tumor or an immortalized hepatocyte, a hepatic progenitor cell such as derived from a pluripotent stem cell, a multipotent stem cell or a cell isolated from pre-term liver tissue, a transdifferented liver cell (a cell derived from a transdifferentiated cell, i.e., cells from tissue other than liver). In embodiments, primary hepatocytes are freshly isolated or are cryopreserved prior to use in cell culture.

As used herein, "have," "having," "include," "including," "comprise," "comprising," or the like are used in their open ended sense, and generally mean "including, but not limited to." It will be understood that "consisting essentially of," "consisting of," and the like are subsumed in "comprising" and the like.

A compound referred to herein, includes salts, isomers, hydrates, solvates, and polymorphs of the specifically referenced compound.

The present disclosure describes, among other things, compounds, compositions, and methods that can enhance global drug metabolism of cultured liver cells. As used herein, to enhance "global drug metabolism" means to increase levels of two or more drug metabolism enzymes (e.g., three of more, four or more, five or more, six or more, seven or more, etc.). In embodiments, the two or more drug metabolism enzymes can be enzymes from different pathways to distinguish from typical drug metabolism inducers that induce a given enzyme or enzymes within a given pathway. The levels of the enzymes that are increased can be the levels of the enzyme, mRNA expressing the enzyme, or enzyme activity. The levels of one or more of the enzymes can be increased by any appreciable amount, such as about 5% or greater (e.g., about 10% or greater, about 20% or greater, about 30% or greater, about 40% or greater, or about 50% or greater), relative to liver cells cultured under substantially similar conditions but not in the presence of the compound that enhances drug metabolism. It will be understood that "substantially similar conditions" means as similar as practicable, such as the same or similar temperature, gas ratio, culture medium (absent the "enhancing" compound), and the like.

Drug metabolism enzymes whose levels can be increased include phase I drug metabolism enzymes, phase II drug metabolism enzymes, and phase III drug metabolism enzymes. Phase I enzymes include cytochrome P450 monooxygenase (CYP) enzymes, flavin-containing enzymes, alcohol dehydrogenase, aldehyde dehydrogenase, monoamine oxidases, NADPH-cytochrome P450 reductases, esterases, amidases, epoxide hydrolases, and the like. Phase II drug metabolism enzymes, which are generally enzymes that catalyze conjugation, include methyltransferases, sulfotransferases (SULT), N-acetyltransferases, bile acid-CoA: amino acid N-acetyltransferases, UDP-glucuronosyltransferases (UGT), glutathione S-transferases (GST), acetyl coA carboxyltransferases, and the like. Phase III drug metabolism enzyme, which generally export compounds from cells, include ATP-binding cassette (ABC) transporters, solute carriers (SLC), and the like. In embodiments described herein, the levels of two or more CYP enzymes (e.g., three of more, four or more, five or more, six or more, seven or more, etc.) are increased in liver cells cultured in the presence of an "enhancing" compound described herein.

Non-limiting examples of specific enzymes whose levels can be increased include ABCB1, ABCB11, ABCB4, ABCC1, ABCC2, ABCC3, ABCC4, CYP1A1, CYP1A2, CYP2A6, CYPB6, CYP2C19, CYP2C8, CYP2C9, CYP2D6, CYP3A4, CYP3A43, CYP3A5, CYP3A7, CYP4F12, SLC01A1, SLC2A1, SLCO1B1, SLCO2B1, SULT1A1, SULT1A2, SULT1A3, SULT1B1, SULT1E1, SULT2A1, UGT1A1, UGT1A6, UGT1A8, UGT2B15, UGT2B4, GSTA2, and the like.

Liver cell function is controlled, in part, by the expression of hepatic transcription factors, e.g., HNF1, HNF4, HNF6, C/EBP alpha, C/EBP beta. For example, hepatocyte nuclear factor 4-alpha (HNF4alpha) is a nuclear receptor (NR) required for liver development and for controlling the expression of many hepatic-specific genes associated with important metabolic pathways, e.g., drug metabolism, cholesterol and fatty acid metabolism, glucose homeostasis and inflammation. Other transcription factors are directly involved with controlling the expression of many of the Phase I, Phase II and Phase III drug metabolism genes which determine the metabolism, disposition and toxicity of a drug. DME related genes include aryl hydrocarbon receptor (AHR), pregnenolone x-receptor (PXR), constitutive androstene receptor (CAR) and RXR (retinoid X receptor). An enhancement of global hepatic function following exposure to the "enhancing" compound can result from enhancement of one or more transcription factors Non-limiting examples of transcription factors whose levels can be increased by exposure to the 'enhancing" compound include HNF1, HNF4, HNF6, C/EBP alpha, C/EBP beta, Ahr, CAR, PXR, and RXR.

An enhancement of global hepatic function following exposure to the "enhancing" compound can result from enhancement of one or more transcription factors or by modulating the complex interactions of transcription factors that determine cell function. For example, HNF4 acts as a direct transactivator of numerous drug metabolizing cytochrome P450 (CYP) genes, suggesting that this factor is a global regulator which supports CYP transcription in the liver. Complex interactions and cross-talks between HNF4 and other transcription factorsimpact the of many of the Phase I, II and III drug metabolism genes. For example, HNF4 modulates Phase I CYP expression in the liver by interacting with CAR, PXR, the glucocorticoid receptor (GR), the feeding-fasting cycle target PGC-1 alpha, other liver-enriched factors, such as C/EBPs.

An enhancement of global hepatic function following exposure to the "enhancing" compound can result from modulating the complex interactions of transcription factors that determine cell function. Non-limiting examples of specific transcription factors whose interactions can be modulated in a manner to increase global hepatic function following exposure to the "enhancer" compound include hepatic nuclear factors (HNF1, HNF4, HNF6, C/EBP alpha, C/EBP beta), forkhead box receptors such FOXO proteins (e.g., FOXO1, FOXO3, FOXA1, FoxA2, FOXA3 that modulate glucose metabolism, vitamin D receptor (VDR), and retinoic acid receptors (RAR and RXR), aryl hydrocarbon receptor (AHR), pregnenolone x-receptor (PXR), constitutive androstene receptor (CAR), Accordingly, the compounds and compositions described herein can also serve to enhance hepatic functions other than drug metabolism. In addition, the compounds and compositions described herein can serve to promote differentiation of cultured stem cells into hepatocytes.

The function of transcription factors is controlled in part by co-activators such as steroid receptor coactivators (SRC) SRC1, SRC2, SRC3, or peroxisome proliferator-activated receptor gamma coactivator-1α (PGC1 alpha), and co-inhibitors, e.g., silencing mediator of retinoid and thyroid receptor (SMRT) and nuclear receptor co-repressor (N-CoR). For example, PXR is basally repressed and is activated in a ligand and tissue specific manner through a complex shift in co-repressor (Silencing mediator of retinoid and thyroid receptor (SMRT) and nuclear receptor co-repressor (N-CoR)) and co-activator (Steroid receptor coactivator-1(SRC-1), PPAR and glucocorticoid receptor coactivator-1(PGC-1), Hepatocyte nuclear factor 4 (HNF-4)) interactions favoring activation.

An enhancement of global hepatic function following exposure to the "enhancing" compound can result from modulating the complex interactions of transcription factors, coactivators and coinhibitors that determine cell function.

One compound that can be used to enhance global drug metabolism of cultured liver cells, to promote differentiation of cultured stem cells into hepatocytes, or the like is LFM-A13, [α-Cyano-β-Hydroxy-β-Methyl-N-(2,5-Dibrobophenyl)Propenamide], which has the chemical structure of Formula I:

I

LFMA-13 has been reported to be a potent BTK inhibitor. See, e.g., U.S. Pat. No. 6,303,652 to Uckun et al., which patent is hereby incorporated herein by reference in its entirety to the extent that it does not conflict with the present disclosure. In U.S. Pat. No. 6,303,652 discloses a variety of BTK inhibitors that are structurally similar to LFM-A13. By way of example, based on the teachings of U.S. Pat. No. 6,303,652, one would expect compounds according to Formula II below to have BTK activity.

II where $R_1$ is (i) $(C_1-C_3)$alkyl, (ii) $(C_1-C_3)$cycloalkyl, (iii) phenyl optionally substituted with one or more substituents independently selected from halo, nitro, cyano, hydroxyl, trifluoromethyl, trifluoromethoxy, $(C_1-C_3)$alkoxy, $(C_1-C_3)$alkyl, $(C_1-C_3)$alkanoyl, —$S(O)_2R_c$, or $NR_aR_b$, or (iv) $NR_aR_b$;

$R_2$ is hydroxyl, $(C_1-C_6)$alkoxy, $(C_1-C_6)$alkanoxy amino $(C_2-C_5)$alkoxy; hydroxy $(C_2-C_5)$alkoxy amino $(C_2-C_5)$alkanoxy, or hydroxyl $(C_2-C_5)$alkanoxy;

$R_3$ is cyano or $(C_1-C_3)$alkanoyl;

$R_4$ is hydrogen, $(C_1-C_3)$alkyl, hydroxyl $(C_2-C_5)$alkyl, or amino $(C_2-C_5)$alkyl;

$R_a$ and $R_b$ are each independently hydrogen, or $(C_1-C_3)$alkyl, or $R_a$ and $R_b$ together with the nitrogen to which they are attached are pyrrolidino, piperidino, morpholino, or thiomorpholino;

n and m are independently an integer from 0-2;

X is halo;

Y is —$S(O)_2R_c$ or —$OR_c$; and $R_c$ is (i) $(C_1-C_3)$alkyl, unsubstituted or substituted with halo, or (ii) aryl.

While the inventors of the present subject matter have found that BTK inhibitors that are structurally unrelated to LFM-A13 did not enhance global metabolism function of cultured liver cells, it is believed that compounds according to Formula II, which are structurally and functionally (at least with respect to BTK inhibition) similar to LFM-A13, can have effects similar to LFMA-13 on enhancement of global drug metabolism or enhancement of hepatic function or differentiation.

Accordingly, embodiments of the compositions and methods described herein include compounds according to Formula II. In embodiments, $R_1$ of Formula II is $(C_1-C_3)$alkyl or $(C_1-C_3)$cycloalkyl. In embodiments, $R_2$ of Formula II is hydroxyl or $(C_1-C_6)$alkoxy. In embodiments, $R_3$ of Formula II is cyano. In embodiments, $R_4$ of Formula II is hydrogen or $(C_1-C_3)$alkyl. In embodiments, m of Formula II is 0. In embodiments, n of Formula II is 2. In embodiments, X of Formula II is Br. In embodiments, Y of Formula II is —$S(O)_2R_c$, where $R_c$ is $(C_1-C_3)$alkyl.

In embodiments, the compounds and compositions described herein include compounds according to Formula III, which is a subset of Formula II:

III where n and m are independently an integer from 0-2,

X is halo,

Y is —$S(O)_2R_c$ or —$OR_c$, and $R_c$ is (i) $(C_1-C_3)$alkyl, unsubstituted or substituted with halo, or (ii) aryl.

In embodiments, m of Formula III is 0. In embodiments, n of Formula III is 2. In embodiments, X of Formula II is Br. In embodiments, Y of Formula II is —$S(O)_2R_c$, where $R_c$ is $(C_1-C_3)$alkyl.

In embodiments, the compounds and compositions described herein include LFMA-13, [α-Cyano-β-Hydroxy-β-Methyl-N-(2,5-Dibrobophenyl)Propenamide], Formula I.

A compound according to Formula II, which includes compounds according to Formulas I and III, can be included as a component of a composition for culturing cells, such as liver cells or stem cells, or can be added to cell culture medium. The composition can be included as a component in, or added to, any suitable cell culture medium. Non-limiting examples of cell culture media to which a compound according to Formula II can be included or added include Eagles Basal Medium (BME); Eagle's Minimum Essential Medium, also called Modified Eagle's Medium (MEM); Dulbecco's Modified Eagle's Medium (DMEM); and the like.

By way of example, a cell culture composition for culturing mammalian cells, such as liver cells or stem cells, can include one or more amino acids (and often all 20 of the amino acids from which proteins are synthesized); one or more purine, such as hypoxanthine, and one or more pyrimidine, such as thymidine, for synthesis of nucleotides or RNA or DNA, or one or more nucleotides; one or more precursors for synthesis of phospholipids, such as choline and inositol; one or more vitamins, particularly those which serve as part of coenzymes; glucose as an energy source or another suitable energy source; or one or more various inorganic ions, such as $Na^+$, $K^+$, $Ca^{2+}$, $Cu^{2+}$, $Zn^{2+}$, and $Co^{2+}$, which can be provided via salts. Preferably, the composition has a pH and salt concentration that simulates an in vivo environment.

A cell culture composition can also include antibiotics, proteins or polypeptides, serum or the like. In embodiments, the cell culture composition is a chemically-defined composition. As used herein, "chemically-defined medium" means cell culture media that contains no components of unknown composition. Chemically defined cell culture media can, in various embodiments, contain no proteins, hydrolysates, or peptides of unknown composition. In some embodiments, chemically defined media contains polypeptides or proteins of known composition, such as recombinant growth hormones. Because all components of chemically-defined media have a known chemical structure, variability in culture conditions and thus variability in cell response can be reduced, increasing reproducibility. In addition, the possibility of contamination is reduced. Further, the ability to scale up is made easier due, at least in part, to the factors discussed above.

A cell culture medium can include a compound according to Formula II in any suitable concentration. If it is desired to enhance, e.g., global drug metabolism, the compound to Formula II can be added at a concentration effective to cause the enhanced levels of two or more drug metabolism enzymes (e.g., as discussed above), relative to cells cultured in substantially similar conditions. In embodiments, the compound of Formula II is present in the composition at a concentration of less than about 500 micromolar, such as less than about 250 micromolar, less than about 100 micromolar, less than about 50 micromolar, or less than about 20 micromolar. Generally, the compound of Formula II is present in the composition at a concentration of greater than about 0.001 micromolar, such as greater than about 0.005 micromolar, greater than about 0.01 micromolar, or greater than 0.05 micromolar. In embodiments, the compound of Formula I is present in the composition from a concentration of about 0.05 micromolar to about 100 micromolar, such as from about 0.01 micromolar to about 50 micromolar, or from about 1 micromolar to about 20 micromolar, or about 10 micromolar.

A compound according to Formula II can be added to a cell culture composition in any suitable manner. By way of example, a stock solution containing a compound according to Formula II can be made by dissolving the compound in an appropriate solvent, such as DMSO or the like. The stock solution can be made at any fold higher concentration than the desired concentration of the resulting cell culture medium once added. By way of example, the stock solution can be a 1000-fold concentration solution, a 2000-fold concentration solution, or the like. The stock solution can be added to cell culture medium, which can be a commercially available medium or other medium, to achieve the appropriate desired concentration. The prepared medium can then be sterilized via any suitable process, such as by filtration using a 0.2 micron filter. The medium can be used immediately or stored as appropriate, e.g., at 4° C.

Cells can be cultured in cell culture medium that includes a compound of Formula II or to which a compound of Formula II is added. Cell culture techniques and procedures known in the art can be employed. By way of example, cells can be harvested prior to seeding and suspended in a suitable medium, such as a culture medium in which the cells are to be cultured once seeded. For example, the cells can be suspended in a culture medium containing the compound of Formula II or in a culture medium to which a compound of Formula II can later be added.

The cells can be seeded at any suitable concentration. Typically, the cells are seeded at about 10,000 cells/cm$^2$ to about 500,000 cells/cm$^2$ of surface area of the cell culture device employed. For example, cells can be seeded at about 50,000 cells/cm$^2$ to about 150,000 cells/cm$^2$ of surface area of the cell culture device employed. However, higher and lower concentrations can readily be used. The incubation time and conditions, such as temperature, $CO_2$ and $O_2$ levels, culture medium composition, and the like, will depend on the nature of the cells being cultured and can be readily modified. The amount of time that the cells are cultured can vary depending on the cell response desired.

The cultured cells can be used for any suitable purpose, including (i) investigational studies or for developing therapeutic uses, (ii) for investigational studies of the cells in culture, (iii) for developing therapeutic uses, (iv) for therapeutic purposes, (v) for studying gene expression, (vi) for studying drug and toxicity screening, and (vii) the like.

The presence of a compound according to Formula II can enhance the general function of liver cells, can enhance global drug metabolism of cultured liver cells, can promote differentiation or maintenance of hepatic cells, or the like.

In embodiments, the cultured cells are used for studying metabolism of candidate drug compounds. Preferably, the cultured cells are liver cells, such as primary human hepatocytes or cells from liver cell lines or cells derived from stem cells. The drug metabolism function of the liver cells can be enhanced by culturing the cells in the presence of a compound according to Formula II. The candidate compound can be added to the cell culture, and the effects of drug metabolism on the candidate compound can be tested. Any suitable method for determining the effects of drug metabolism can be employed. By way of example, supernatant from the culture medium after addition of the candidate compound can be removed and subjected to analysis (e.g., HLPC, gas chromatograph, mass spectrometry, NMR, or the like, or combinations thereof) to determine the composition of metabolites produced by culture. The identified metabolites can be concentrated or synthesized and tested for toxicity in culture or animals as generally known in the art. The effects of the candidate compound and any metabolites produced during culture on the cultured liver cells can be studied. For example, enzyme assays (e.g., for drug metabolism enzyme induction), gene expression (e.g., mRNA analysis), toxicity analysis, or the like can be performed on the cultured liver cells.

The candidate compound can be added to the culture at any suitable time. In embodiments, the candidate compound is added to the culture after the cells have been incubated in a medium containing a compound of Formula II for a time sufficient to enhance global drug metabolism. In embodiments, the candidate compound is added to the cell culture after the cells have been cultured in the presence of a compound according to Formula II for at least about 30 minutes. In embodiments, the candidate compound and the compound according to Formula II are presented to cells at the same time. For example, the candidate compound can be added to cell culture medium containing a compound according to Formula II and the resulting medium can then be used to culture the cells. Alternatively, the candidate compound and the compound according to Formula II can be added to cell culture medium or cell culture at the same time.

In embodiments, cells are cultured in a medium including a compound according to Formula II to promote viral infection of cells. Said infected cells can be used to screen for antiviral drugs or used to produce vaccines. Preferably, the cultured cells are liver cells, such as primary human hepatocytes or cells from liver cell lines or cells derived from stem cells. The global function of the liver cells can be enhanced by culturing the cells in the presence of a compound according to Formula II. The virus can be added to the cell culture, and the effects of the compound on the virus or the virus on the cells in the presence of the compound can be assessed. Any suitable method for determining the effects of the virus or the compound can be employed. By way of example, infection rate, infection density, or the like can be determined. Cellular or viral gene expression, mRNA, or proteins can be assayed.

In embodiments, cells are cultured in a medium including a compound according to Formula II to engineer liver tissue. The cells can be, or include, primary hepatocytes or stem cells. The presence of the compound according to Formula II would be expected to facilitate differentiation towards hepatocytes or maintain hepatocyte function.

In embodiments, cells are cultured in a medium including a compound according to Formula II to generate a liver assistant device (e.g., a device to bridge patient to liver transplantation) or to generated cells for use in a liver cell transplantation. The cells can be, or include, primary hepatocytes or stem cells. The presence of the compound according to Formula II would be expected to facilitate differentiation towards hepatocytes or maintain or enhance hepatocyte function.

In embodiments, cells are cultured in a medium including a compound according to Formula II to enhance expression of hepatocyte derived therapeutic proteins. The therapeutic proteins can be isolated from the culture and used for therapeutic purposes. Examples of hepatocyte derived therapeutic proteins whose expression can be enhanced in the presence of a compound according to Formula II include but are not limited to albumin, fibrinogen, lipoproteins, ceruloplasmin, transferrin, complement, glycoproteins, etc. Cells cultured in the presence of a compound according to Formula II to express such hepatocyte derived therapeutic proteins can be, or include, primary hepatocytes or stem cells.

In embodiments, stem cells are cultured in a medium containing a compound according to Formula II to facilitate differentiation to hepatocytes or maintain hepatocyte function.

A number of embodiments of compositions and methods are described herein. A summary of selected aspects of such compositions and methods is provided below.

In a first aspect a composition for culturing cells includes a compound having a structure of formula II:

where $R_1$ is (i) $(C_1\text{-}C_3)$alkyl, (ii) $(C_1\text{-}C_3)$cycloalkyl, (iii) phenyl optionally substituted with one or more substituents independently selected from halo, nitro, cyano, hydroxyl, trifluoromethyl, trifluoromethoxy, $(C_1\text{-}C_3)$alkoxy, $(C_1\text{-}C_3)$alkyl, $(C_1\text{-}C_3)$alkanoyl, —S(O)$_2$R$_c$, or NR$_a$R$_b$, or (iv) NR$_a$R$_b$;

$R_2$ is hydroxyl, $(C_1\text{-}C_6)$alkoxy, $(C_1\text{-}C_6)$alkanoxy amino $(C_2\text{-}C_5)$alkoxy; hydroxy $(C_2\text{-}C_5)$alkoxy amino $(C_2\text{-}C_5)$alkanoxy, or hydroxyl $(C_2\text{-}C_5)$alkanoxy;

$R_3$ is cyano or $(C_1\text{-}C_3)$alkanoyl;

R4 is hydrogen, $(C_1\text{-}C_3)$alkyl, hydroxyl $(C_2\text{-}C_5)$alkyl, or amino $(C_2\text{-}C_5)$alkyl;

$R_a$ and $R_b$ are each independently hydrogen, or $(C_1\text{-}C_3)$ alkyl, or $R_a$ and $R_b$ together with the nitrogen to which they are attached are pyrrolidino, piperidino, morpholino, or thiomorpholino;

n and m are independently an integer from 0-2;

X is halo;

Y is —S(O)$_2$R$_c$ or —OR$_c$; and $R_c$ is (i) $(C_1\text{-}C_3)$alkyl, unsubstituted or substituted with halo, or (ii) aryl.

The composition can also include one or more component of cell culture, such as an energy source for the cells, an amino acid, vitamins, or the like. The compound can be present in the composition in an amount sufficient to enhance metabolic function of cultured liver cells.

A second aspect is a composition according to the first aspect, wherein the compound has a structure of formula III:

where n and m are independently an integer from 0-2,
X is halo,
Y is —S(O)$_2$R$_c$ or —OR$_c$, and
$R_c$ is (i) $(C_1\text{-}C_3)$alkyl, unsubstituted or substituted with halo, or (ii) aryl.

A third aspect is a composition according to the first or second aspects, wherein m is 0.

A fourth aspect is a composition according to any of the first three aspects, wherein n is 2.

A fifth aspect is a composition according to the first aspect, wherein the compound is LFM-A13.

A sixth aspect is a composition according to any of aspects 1-5, wherein the compound is present in the composition at a concentration from about 0.1 micromolar to about 50 micromolar.

A seventh aspect is a composition according to any of aspects 1-5, wherein the compound is present in the composition at a concentration from about 1 micromolar to about 20 micromolar.

An eighth aspect is a composition according to any aspects 1-7, wherein the composition comprises serum.

A ninth aspect is a composition according to any of aspects 1-7, wherein the composition is free from serum.

A tenth aspect is a composition according to any of the preceding aspects, further comprising liver cells.

An eleventh aspect is a composition according to the tenth aspect, wherein the liver cells are hepatocytes.

A twelfth aspect is a composition according to the eleventh aspect, wherein the hepatocytes are primary hepatocytes.

A thirteenth aspect is a composition according to any of the preceding aspects, further comprising stem cell-derived hepatocytes.

A fourteenth aspect is a composition according to any of the preceding aspects, further comprising a second compound, wherein the second compound is a candidate compound for which metabolites are desired to be analyzed.

A fifteenth aspect is a composition according to any of the preceding aspects, further comprising a virus capable of infecting cultured liver cells.

A sixteenth aspect is a method for enhancing the metabolic function of liver cells in culture, comprising: (i) culturing liver cells in a composition according to any of aspects 1-9, wherein the compound is present in an amount effective to enhance levels of more than one CYP enzyme in the cultured liver cells relative to liver cells cultured in a substantially similar medium but lacking the compound according to formula II.

A seventeenth aspect is a method according to the sixteenth aspect, wherein the liver cells are hepatocytes.

An eighteenth aspect is a method according to the seventeenth aspect, wherein the hepatocytes are primary hepatocytes.

A nineteenth aspect is a method according to the sixteenth aspect, wherein the liver cells are differentiated stem cells.

A twentieth aspect is a method according to any one of aspects 16-19, further comprising isolating from the composition proteins secreted from the liver cells.

A twenty-first aspect is a method according to any one of aspects 16-19, further comprising isolating a liver cell from the culture and incorporating the cell into a liver assist device.

A twenty-second aspect is a method according to any one of aspects 16-19, further comprising isolating a liver cell from the culture and transplanting the isolated cell into a liver of a subject in need thereof A twenty-third aspect is a method for identifying metabolites of a candidate compound, comprising: (i) culturing liver cells in a composition according to any of aspects 1-9, wherein the compound is present in an amount effective to enhance levels of more than one CYP enzyme in the cultured liver cells relative to liver cells cultured in a substantially similar composition but lacking the compound according to formula II; (ii) contacting the cultured cells with the candidate compound; and (iii) identifying metabolites of the candidate compound.

A twenty-fourth aspect is a method according to the twenty-third aspect, wherein the liver cells are cultured in the composition according to any of aspects 1-9 for a period of time sufficient to enhance drug metabolism enzyme levels prior to contacting the cultured cells with the candidate compound.

A twenty-fifth aspect is a method according to aspect 23 or 24, wherein the liver cells are cultured in the in the composition according to any of aspects 1-9 for about 30 minutes prior to contacting the cultured cells with the candidate compound.

A twenty-sixth aspect is a method according to any of aspects 23-25, wherein the liver cells are hepatocytes.

A twenty-seventh aspect is a method according to the twenty-sixth aspect, wherein the hepatocytes are primary hepatocytes.

A twenty-eights aspect is a method for promoting differentiation of stem cells to hepatocytes, comprising culturing stem cells in a composition according to any of aspects 1-9.

In the following, non-limiting examples are presented, which describe various embodiments of representative compositions and methods for enhancing global hepatic function.

EXAMPLES

Example 1

Effects of LF, LFM and LFM-A13 on CYP Enzyme Levels on Cultured Liver Cells

Effects of leflunomide (LEF), leflunomide metabolite (LFM), and the leflunomide metabolite analog A-13 (LFMA-13), on CYP3A4 and CYP1A2 function in primary human hepatocytes are tested. Briefly, primary human hepatocytes cultured on collagen I coated surface are incubated with Corning hepatocyte medium containing vehicle control, 10 µM LF, 10 µM LFM and 10 µM LFM-A13, respectively. At the end of 48-hour incubation, CYP3A4 and CYP1A2 enzymatic assays are performed using Promega P450-Glo™ assay kit. Assay results are normalized to the ATP level in the same well. The results are presented in FIG. 1.

Figure 1:
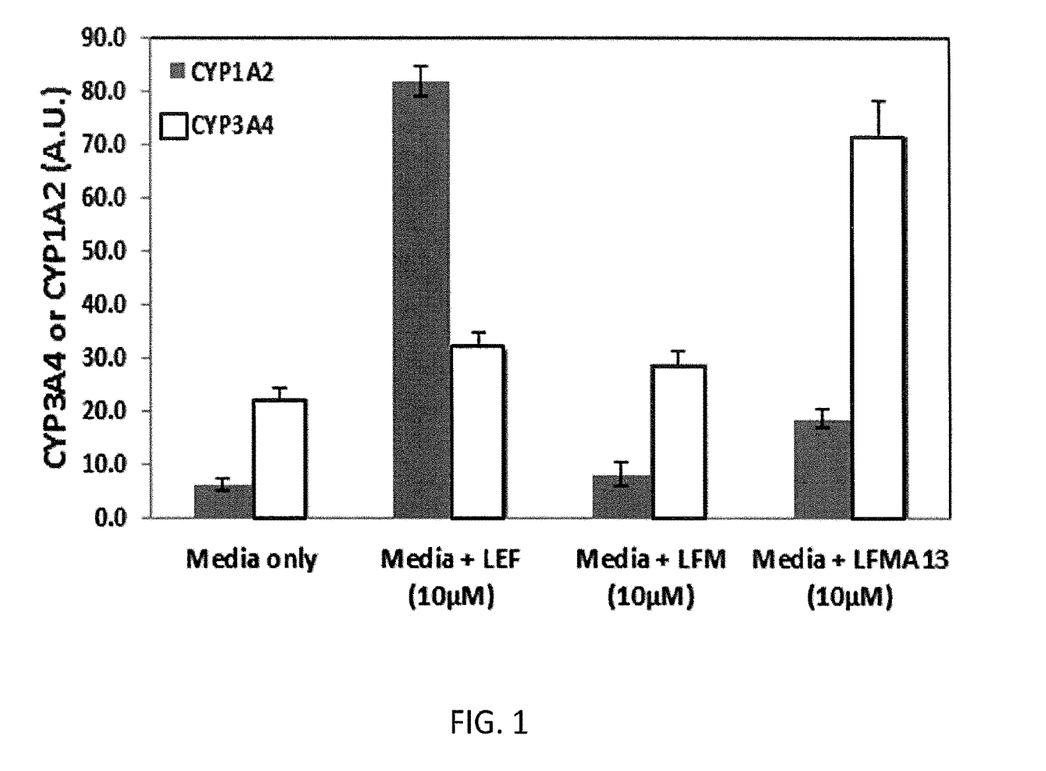
FIG. 1 is a bar graph showing the effect of leflunomide (LEF), leflunomide metabolite (LFM) and leflunomide metabolite analog A13 (LMF-A13) relative to control (Media only) on CYP3A4 or CYP1A2 activity in cultured primary human hepatocytes.

As shown in FIG. 1, LEF has little effect on CYP3A4 activity, but increased CYP1A2 activity by about 12-fold consistent with literature reports indicating that LEF is a CYP1A2 inducer. LFM has little effect on CYP3A4 and CYP1A2 activity. LFM-A13 produced the greatest increase in CYP3A4 activity (about 4-fold increase) and also enhanced CYP1A2 activity (about 3-fold).

The effect of these compounds on CYP3A4 activity is also tested on liver cell lines. Briefly, HepaRG cells (Invitrogen) and Corning liver cell lines cultured on collagen I coated surface are incubated with medium containing vehicle control, 10 µM leflunomide (LF), 10 µM LFM and 10 µM LFM-A13, respectively. At the end of 48-hour incubation, CYP3A4 enzymatic assays are performed using Promega P450-Glo™ assay kit. Assay results are normalized to the ATP level in the same well. The results are presented in FIG. 2.

Figure 2:
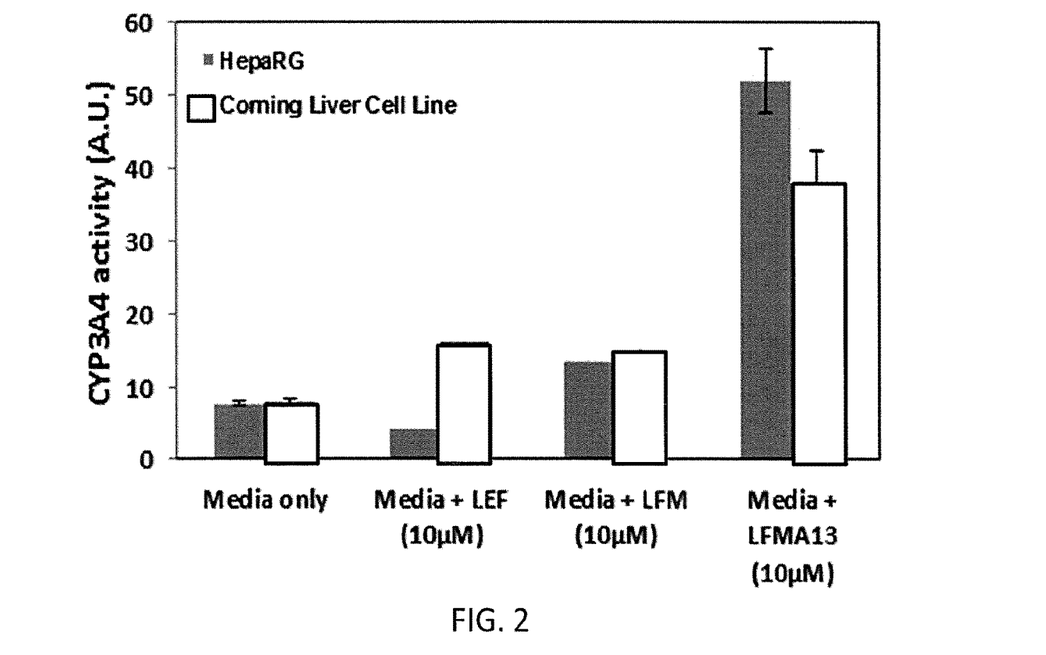
FIG. 2 is a bar graph showing the effect of leflunomide (LF), leflunomide metabolite (LFM) and leflunomide metabolite analog A13 (LMF-A13) relative to control (Media only) on CYP3A4 activity in cultured liver cell lines (HepaRG and Corning Liver Cell Line).

As shown in FIG. 2, the effect of the compounds on CYP3A4 activity in the liver cell lines is similar to the effect in the primary human hepatocytes (compare FIG. 1 to FIG. 2).

The effect of LFM-A13 on CYP3A4 functions in primary human hepatocytes cultured in different media is tested. Briefly, primary human hepatocytes cultured on collagen I coated surface are incubated with five different media (four commercial available hepatocyte medium and Corning hepatocyte medium) containing vehicle and 10 µM LFM-A13, respectively. At the end of 48-hour incubation, CYP3A4 enzymatic assays are performed using Promega P450-Glo™ assay kit. Assay results are normalized to the ATP level in the same well. Results are presented in FIG. 3.

Figure 3:
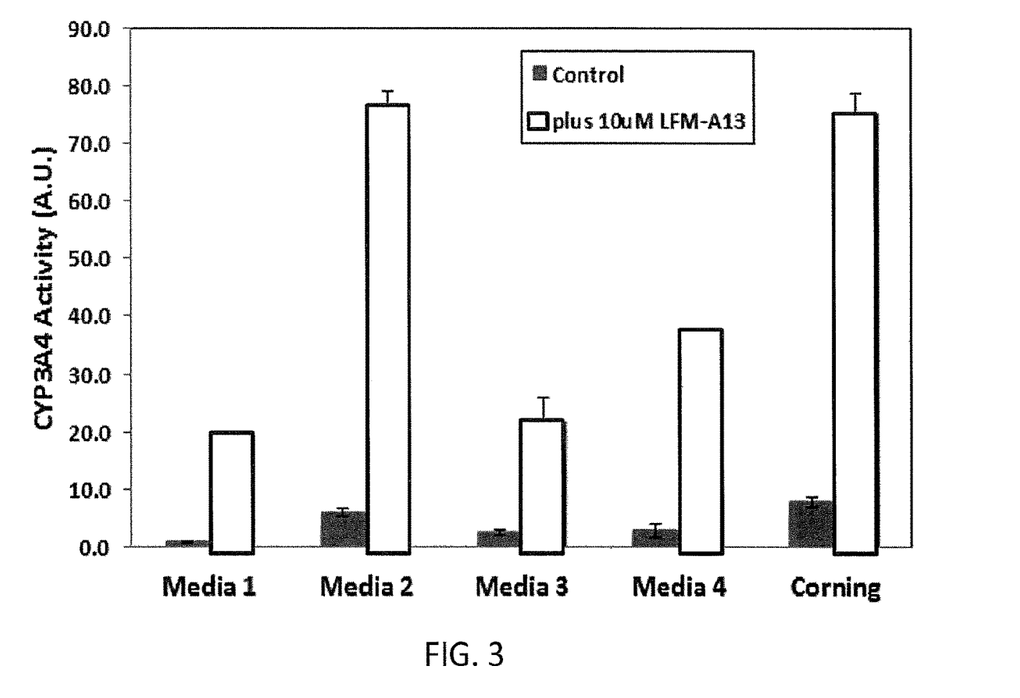
FIG. 3 is a bar graph showing the effect of leflunomide metabolite analog A13 (LMF-A13) relative to control (Media only) on CYP3A4 activity in primary human hepatocytes cultured in five different hepatocyte culture media.

As shown in FIG. 3, LFMA-13 increased CYP3A4 activity in cells cultured in all five of the cell culture media tested.

The effects of leflunomide (LEF), leflunomide metabolite (LFM), and the leflunomide metabolite analog A-13 (LFMA-13) on basal and induced CYP3A4 activity is studied. Briefly, primary human hepatocytes cultured on collagen I coated surface are incubated with Corning hepatocyte medium containing vehicle control, 10 µM LF, 10 µM LFM and 10 µM LFM-A13, respectively, in the presence or absence of 25 µM rifampin, a known CYP3A4 inducer. At the end of 48-hour incubation, CYP3A4 enzymatic assays are performed using Promega P450-Glo™ assay kit. Assay results are normalized to the ATP level in the same well. The results are presented in FIG. 4.

Figure 4:
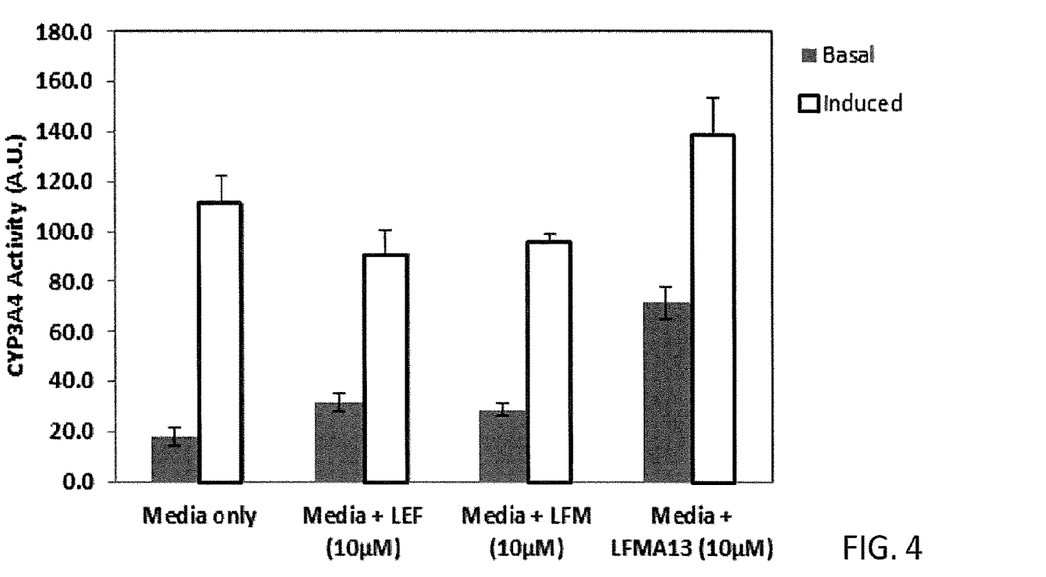
FIG. 4 is a bar graph showing the effect of leflunomide (LEF), leflunomide metabolite (LFM) and leflunomide metabolite analog A13 (LMF-A13) relative to control (Media only) on basal and rifampin (RIF) induced CYP3A4 activity in cultured primary human hepatocytes.

As shown in FIG. 4, neither LEF nor LFM has much of an effect on basal or induced CYP3A4 activity. In contrast, LMF-A13 increased both basal and induced CYP3A4 activity. That LFMA-13 increased induced CYP3A4 activity suggests that LFMA-13 enhances global drug metabolism by a mechanism that is not solely as an inducer of gene expression. While not intending to be bound by theory, it is believed that low concentrations of LFMA-13 (e.g., below about 5 micromolar) can have a post-translational regulational stabilizing effect, such as phosphorylation. While further not intending to be bound by theory, it is also believed that, at higher concentrations (e.g., about 5 micromolar), LFMA-13 induces gene expression of drug metabolism enzymes.

The effects of various concentrations of LFM-A13 are tested on the basal and induced activity of CYP1A2 and CYP3A4. Briefly, primary human hepatocytes cultured on collagen I coated surface are incubated with MFE medium containing vehicle control, 20 µM LFM-A13, 10 µM LFM-A13, 5 µM LFM-A13, 2.5 µM LFM-A13, 1.25 µM LFM-A13, 0.63 µM LFM-A13, 0.32 µM LFM-A13 and 0.16 µM LFM-A13, respectively, in the presence or absence of 25 µM rifampin, a known CYP3A4 inducer or in the presence of absence of 100 µM omeprazole, a known CYP1A2 inducer. At the end of 48-hour incubation, CYP3A4 and CYP1A2 enzymatic assays are respectively performed using Promega P450-Glo™ assay kit. Assay results are normalized to the ATP level in the same well. The results are presented in FIGS. 5A-5B.

Figure 5A:
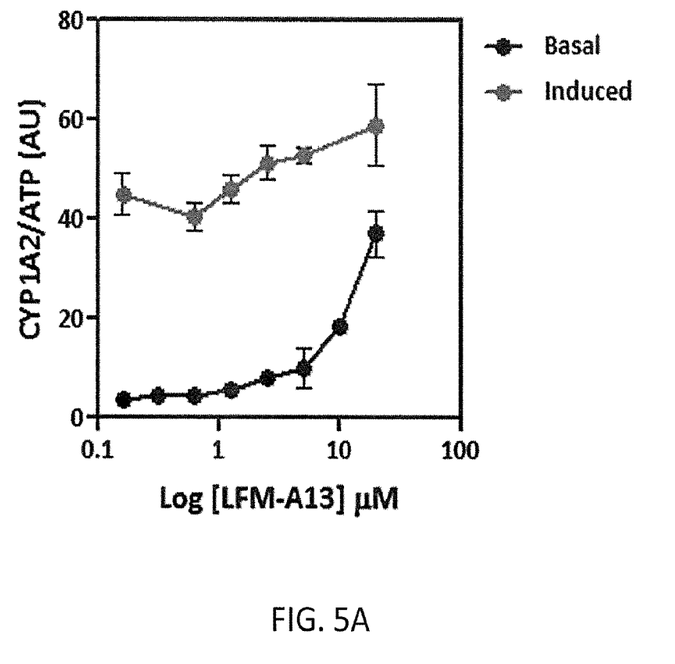
FIGS. 5A-B are plots showing the effect of various concentrations of leflunomide metabolite analog A13 (LMF-A13) on basal and omeprazole induced CYP1A2 activity (A) and basal and rifampin induced CYP3A4 activity (B) in cultured primary human hepatocytes.
Figure 5B:
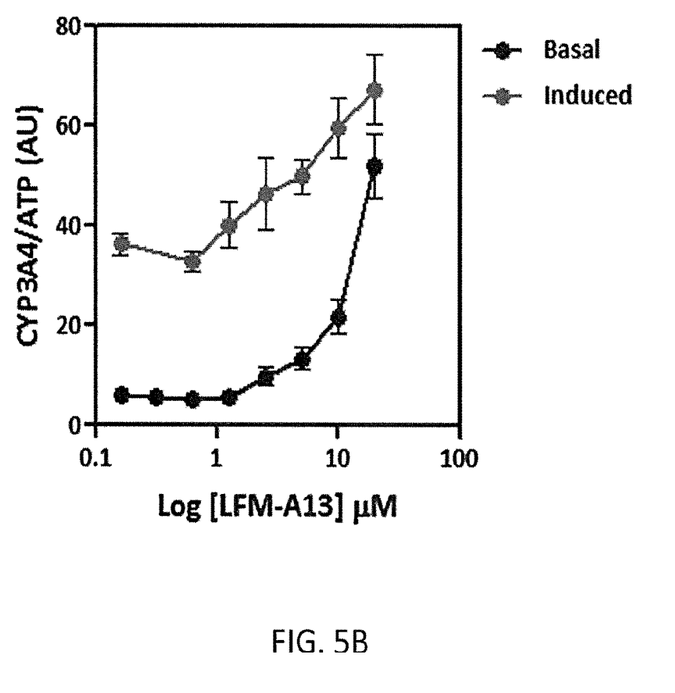

As shown in FIGS. 5A-5B, LFM-A13 enhanced both basal and induced CYP1A2 and CYP3A4 activity. The basal activity is more greatly enhanced at slightly higher concentrations than enhancement of the induced activities.

The effects of LEF, LFM, and LFM-A13 on gene expression are tested. Briefly, primary human hepatocytes cultured on collagen I coated surface are incubated with Corning hepatocyte medium containing vehicle control, 10 µM LEF, 10 µM LFM, and 10 µM LFM-A13, respectively. At the end of 48-hour incubation, total RNA is isolated and relative mRNA levels are quantified using real-time PCR. The results are shown in FIG. 6, where CYP is cytochrome P450 enzyme, SULT is sulfotransferase, UGT is UDP-glucuronosyltransferase, ABC is ATP-binding cassette transporters, AHR is aryl hydrocarbon receptor, CAR is constitutive androstene receptor, and PXR is pregnenolone x-receptor.

Figure 6:
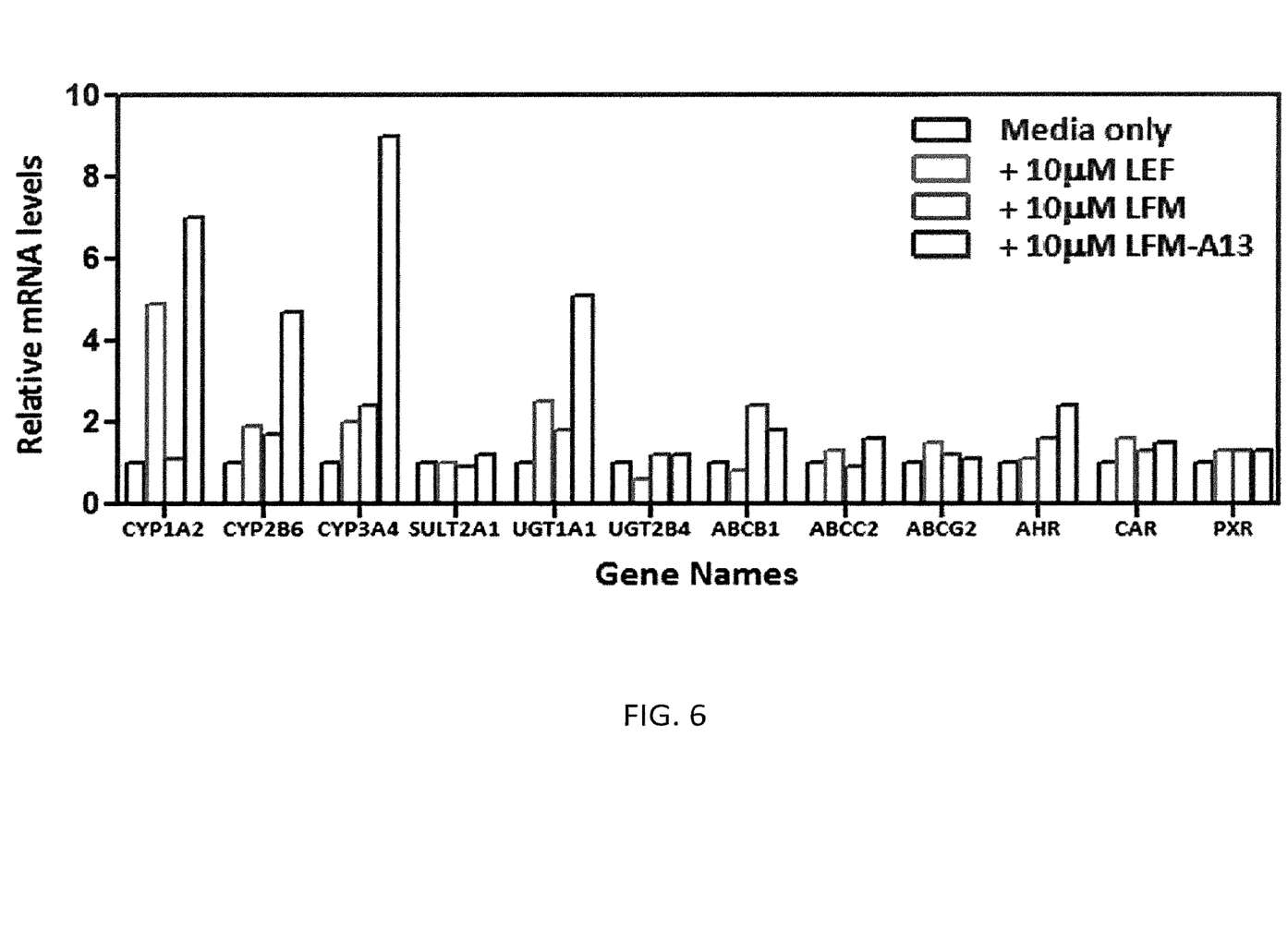
FIG. 6 is a bar graph showing the effect of leflunomide (LEF), leflunomide metabolite (LFM) and leflunomide metabolite analog A13 (LMF-A13) relative to control on mRNA levels for various drug metabolism enzymes and hepatic proteins in cultured primary human hepatocytes. For each mRNA, the results are presented in the following order: control, LEF, LFM, LFM-A13.

As shown in FIG. 6, LFM-A13 greatly increased mRNA levels of all of the CYP enzymes tested (CYP1A2, CYP2B6, and CYP3A4), as well as UGT1A1, some of the ABC transporters and AHR, suggesting that LFM-A13 broadly enhances hepatic function.

The effect of LFMA-13 on levels of mRNA encoding a wider variety of drug metabolism enzymes and other proteins of primary human hepatocytes is tested. Briefly, primary human hepatocytes cultured on collagen I coated surface are incubated with Corning hepatocyte medium containing vehicle control and 10 µM LFM-A13, respectively. At the end of 48-hour incubation, total RNA is isolated and relative mRNA levels are quantified using real-time PCR. The results are shown in FIG. 7, where ABC is ATP-binding cassette transporters, CYP is cytochrome P450 enzyme, SLC is solute carrier transporter, SULT is sulfotransferase, UGT is UDP-glucuronosyltransferase, GST is glutathione S-transferase, AHR is aryl hydrocarbon receptor, FOXO is forkhead box receptors, HNF is hepatic nuclear factor, NCO is nuclear receptor coactivator, NR is nuclear receptor, PPARGC1A is peroxisome proliferator-activated receptor gamma coactivator 1-alpha, RXR is retinoid X receptor, and VDR is vitamin D receptor.

Figure 7:
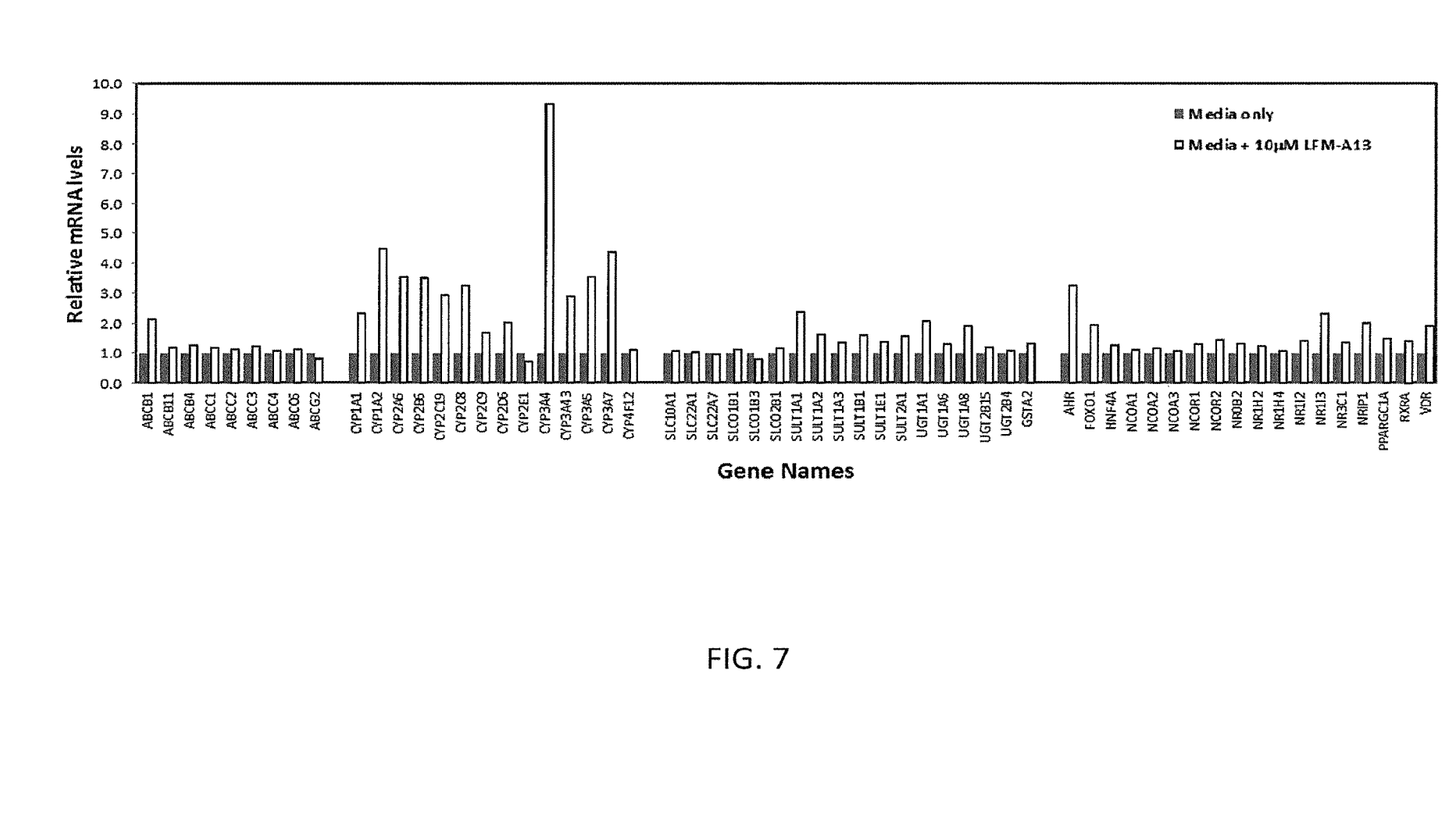
FIG. 7 is a bar graph showing the effect of leflunomide metabolite analog A13 (LMF-A13) relative to control on mRNA levels for various drug metabolism enzymes and hepatic proteins in cultured primary human hepatocytes. For each mRNA, the results are presented in the following order: control, LFM-A13.

As shown in FIG. 7, LFMA-13 appears to have a global effect of enhancing hepatocyte function. A wide variety of drug metabolism enzymes show increased levels in the presence of LFMA-13, including many CYPs. The levels of a number of a number of other hepatic mRNA are also increased in the presence of LFMA-13. These results confirm the broad effect of LFM-A13 on cultured liver cells.

The effects on drug metabolism activity on liver cells is tested for other BTK inhibitors, such as Terreic acid and BTK siRNA. The broad enhancement of hepatic function seen with LFM-A13 is not observed with these structurally unrelated BTK inhibitors.

In addition, since LFM-A13 is also a Polo-like kinase (PLK) inhibitor, the ability of siRNA directed to PLK mRNA to enhance global hepatic function is evaluated. Similar to the BTK inhibitors structurally unrelated to LFM-A13, the Polo-like kinase siRNA did not result in global hepatic enhancement.

Figure 8:
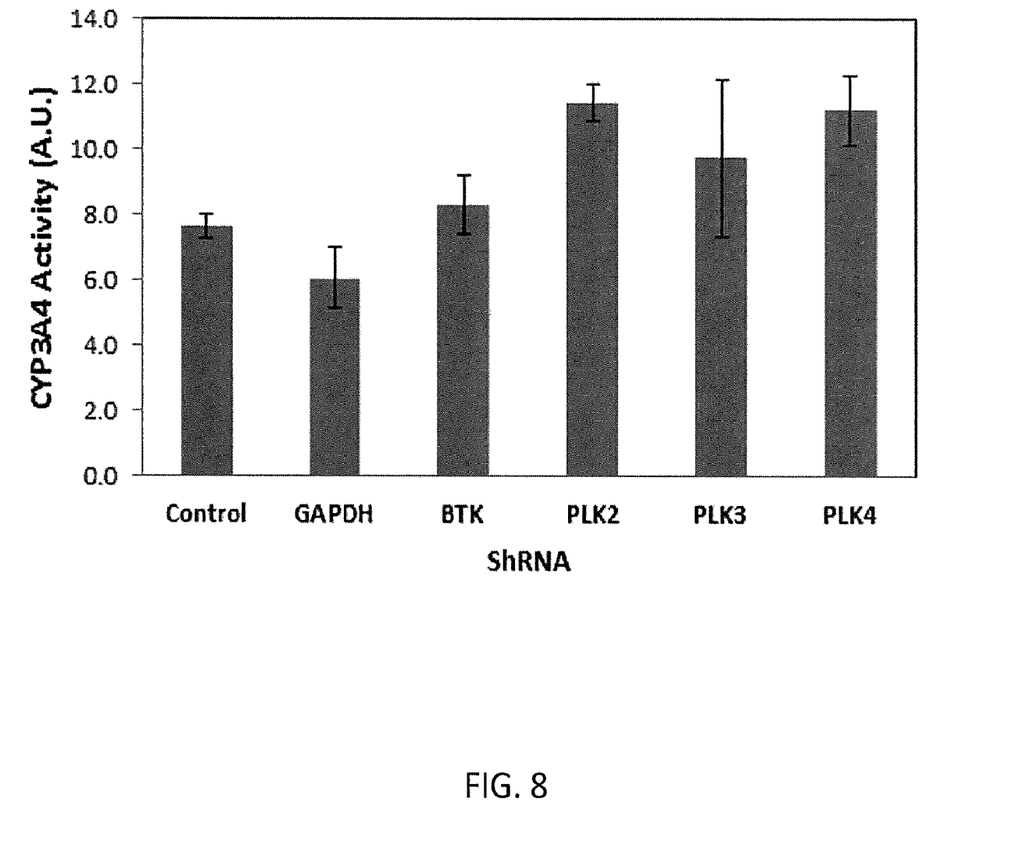
FIG. 8 is a bar graph showing the effect of shRNA directed to Burton's Tyrosine Kinase (BTK) and Polo-like kinase 1(PLK2), PLK3, and PLK4 on CYP3A4 enzymatic activity in cultured primary human hepatocytes.

Results of the effects of shRNA directed to BTK, PLK2, PLK3 and PLK4 on CYP3A4 enzymatic activity are shown in FIG. 8.

Example 2

Effects of LFM-A13 on Differentiation of Stem Cells into Hepatocytes

Figure 9:
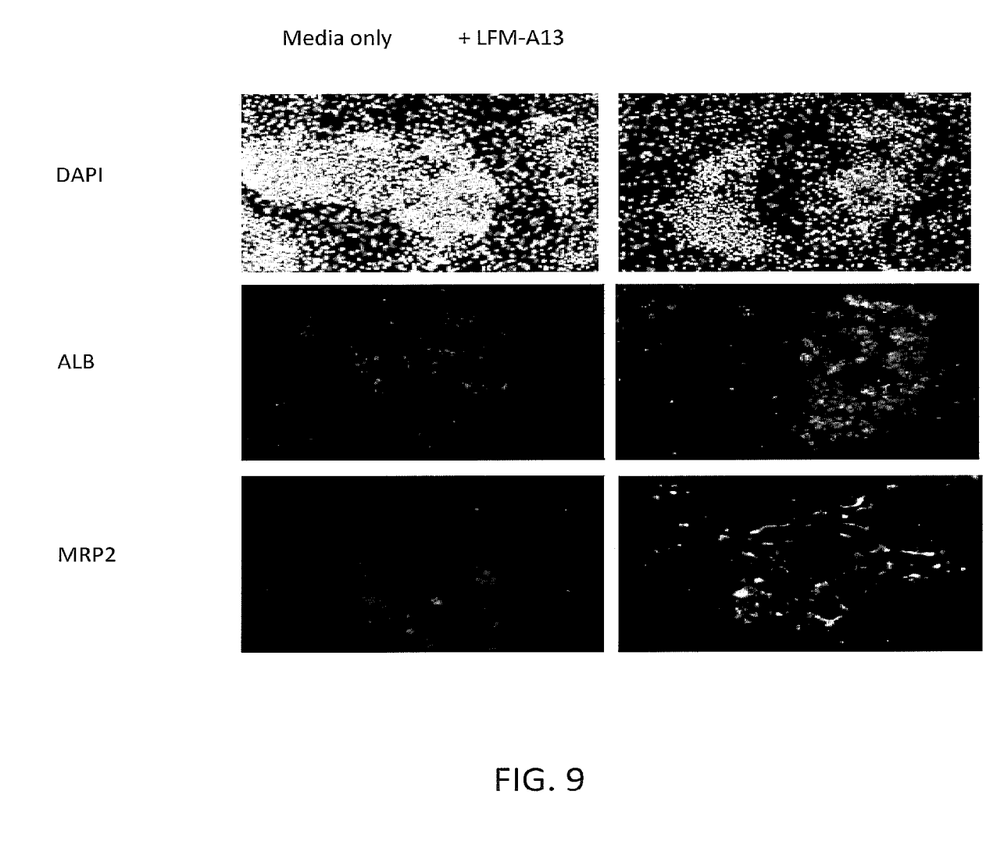
FIG. 9 presents images of fluorescently stained hepatocytes derived from human embryonic stem cells (hESCs) cultured in the presence or absence of LFM-A13. Cell nuclei are stained using 4',6-diamidino-2-phenylindole dihydrochloride (DAN), a marker for stem cells; albumin (ALB), a. hepatic precursor marker; multidrug resistance-associated protein 2 (MRP2), a marker for hepatic function.

The effects of LFM-A13 on human embryonic stem cells (hESCs) derived hepatocytes are evaluated. Briefly, hESCs are committed to the hepatocyte lineage using methods known to those skilled in the art and then are cultured in Corning hepatocyte medium in the presence or absence of 10 µM LFM-A13. After 7 days, the stem cell derived hepatocytes are immunostained with primary antibodies to detect expression of hepatocyte proteins; (b) to test for the presence of albumin (ALB), a hepatic precursor marker; and (c) to test for the presence of multidrug resistance-associated protein 2 (MRP2), a member of the superfamily of ATP-binding cassette (ABC) transporters and a marker for hepatic function. Nuclei of cells are counterestained with 4',6-diamidino-2-phenylindole dihydrochloride (DAPI) to visualize all cells (FIG. a). Results of the immunostaining are shown in FIG. 9. As depicted, hESCs cultured in the absence of LFM-A13 (left column) have low levels of hepatic markers (ALB and MRP2). In contrast, hESCs cultured in the presence of LFM-A13 (right column) have higher levels of hepatic markers (ALB and MRP2). Indicating that LFM-A13 facilitated the differentiation, maintenance, or function of hESCs to hepatocytes.

Figure 10:
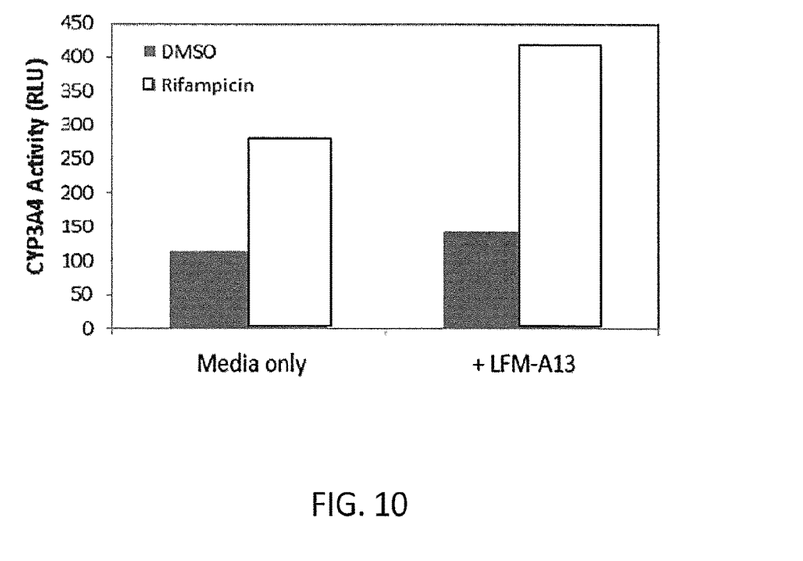
FIG. 10 is a bar graph showing the effect of LFM-A13 on basal and rifampicin induced CYPA4 activity of cultured stem cell derived hepatocytes.
Figure 11:
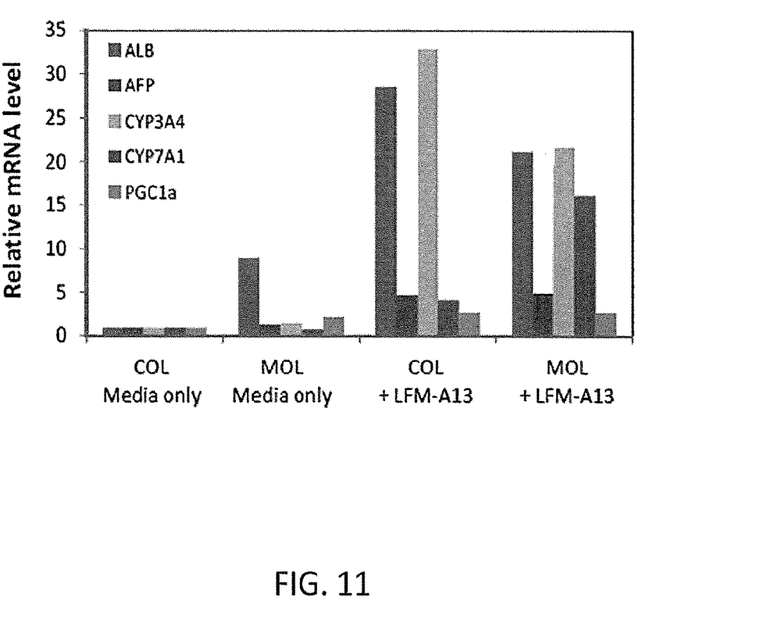
FIG. 11 is a bar graph showing real-time PCR analysis of mRNA expression in hESCs differentiated into hepatic cells or precursors when cells are cultured on collagen coated plates (COL) with or without a Matrigel™ overlay (MOL): ALB is albumin, AFP is alpha-fetoprotein, CYP3A4 is cytochrome P450 3A4, CYP7A1 is cytochrome P450 7A1, and PGC1a is peroxisome-proliferator-activated receptor-gamma co-activator-1 alpha.

The effect of LFM-A13 on rifampicin-induced CYP3A4 activity and on mRNA expression of a variety of hepatic markers is also determined on the differentiated hESCs. As shown in FIG. 10, rifampin-induced CYP3A4 activity is greatly enhanced by the presence of LFM-A13. As shown in FIG. 11, LFM-A13 enhanced expression of a number of hepatic markers. In FIG. 11, ALB is albumin, AFP is alpha-fetoprotein, CYP3A4 is cytochrome p450 3A4, CYP7A1 is cytochrome p450 7A1, and PGC1a is glucocorticoid receptor coactivator-1a (COL=collagen I coated plate; MOL=Matrigel overlay).

Thus, embodiments of CELL CULTURE MEDIUM FOR ENHANCED HEPATOCYTE FUNCTION are disclosed. One skilled in the art will appreciate that the compounds, compositions, and methods described herein can be practiced with embodiments other than those disclosed. The disclosed embodiments are presented for purposes of illustration and not limitation.

What is claimed is:

1. A composition for producing metabolites of a candidate compound in a culture of liver cells, the composition comprising:
   a cell culture medium;
   the liver cells;
   the candidate compound; and
   a compound of Formula:

(LFM-A13)

wherein the LFM-A13 is present in the composition in an amount effective to increase levels of more than one cytochrome P450 monooxygenase (CYP) enzyme by greater than two-fold in the culture of the liver cells relative to liver cells cultured in the same composition but lacking the LFM-A13, and
   wherein the more than one CYP enzyme is chosen from CYP3A4, CYP1A2, or CYP2B6.

2. The composition according to claim 1, wherein the LFM-A13 is present in the composition at a concentration from about 0.1 micromolar to about 50 micromolar.

3. The composition according to claim 1, wherein the LFM-A13 is present in the composition at a concentration from about 1 micromolar to about 20 micromolar.

4. The composition according to claim 1, wherein the cell culture medium comprises serum.

5. The composition according to claim 4, wherein the cell culture medium comprises nutrients capable of supporting cell growth including amino acids, energy sources, and salts, and wherein:
   the energy sources comprise glucose, and
   the salts provide at least one inorganic ion chosen from $Na^+$, $K^+$, $Ca^{2+}$, $Cu^{2+}$, $Zn^{2+}$, and $Co^+$.

6. The composition according to claim 1, wherein the cell culture medium is free from serum.

7. The composition according to claim 1, wherein the liver cells comprise primary hepatocytes.

8. The composition according to claim 1, wherein the liver cells comprise immortalized cells derived from a hepatocyte.

9. The composition according to claim 1, wherein the liver cells comprise a cell line derived from a hepatocyte.

10. The composition according to claim 1, wherein the liver cells comprise a cell line derived from an embryonic stem cell.

11. The composition according to claim 1, wherein the LFM-A13 is present in the composition at a concentration of about 10 micromolar.

12. The composition according to claim 1, wherein the more than one CYP enzyme is CYP3A4 and CYP1A2.

13. The composition according to claim 1, wherein:
   the more than one CYP enzyme is CYP3A4 and CYP1A2; and
   the LFM-A13 is present in the composition in an amount effective to increase levels of the more than one cytochrome P450 monooxygenase (CYP) enzyme by at least three-fold in the culture of the liver cells relative to liver cells cultured in the same composition but lacking the LFM-A13.

14. A method for enhancing the metabolic function of liver cells in culture, comprising:
   culturing the liver cells in the composition according to claim 1, wherein metabolic function of the liver cells is enhanced by the LFM-A13 present in the composition in the amount effective to increase the levels of the more than one CYP enzyme.

15. The method according to claim 14, wherein the liver cells comprise primary hepatocytes.

16. The method according to claim 14, wherein the liver cells comprise immortalized cells derived from a hepatocyte or from an embryonic stem cell.

17. The method according to claim 14, wherein the liver cells comprise a cell line.

18. The method according to claim 17, wherein the cell line is derived from a hepatocyte or from an embryonic stem cell.

19. A method for identifying metabolites of a candidate compound, comprising:
   culturing the liver cells in the composition according to claim 1, wherein the cultured cells are contacted with the candidate compound; and
   identifying the metabolites of the candidate compound.

* * * * *

UNITED STATES PATENT AND TRADEMARK OFFICE
CERTIFICATE OF CORRECTION

PATENT NO. : 10,876,096 B2  
APPLICATION NO. : 14/647304  
DATED : December 29, 2020  
INVENTOR(S) : Ronald Allen Faris et al.

It is certified that error appears in the above-identified patent and that said Letters Patent is hereby corrected as shown below:

On the Title Page

On page 2, in Column 1, item (56), Other Publications, Line 25, delete "Acivation:" and insert -- Activation: --, therefor.

On page 2, in Column 2, item (56), Other Publications, Line 4, delete "Druct" and insert -- Drug --, therefor.

On page 2, in Column 2, item (56), Other Publications, Line 27, delete "Jornal" and insert -- Journal --, therefor.

On page 2, in Column 2, item (56), Other Publications, Line 60, delete "lefluomide" and insert -- leflunomide --, therefor.

On page 2, in Column 2, item (56), Other Publications, Line 62, delete "aldoxines." and insert -- aldoximes. --, therefor.

In the Claims

In Column 18, Line 3, Claim 5, delete "$Co^+$." and insert -- $Co^{2+}$. --, therefor.

Signed and Sealed this  
Sixteenth Day of March, 2021

Drew Hirshfeld  
*Performing the Functions and Duties of the*  
*Under Secretary of Commerce for Intellectual Property and*  
*Director of the United States Patent and Trademark Office*